(12) United States Patent
Wu et al.

(10) Patent No.: US 7,947,485 B2
(45) Date of Patent: *May 24, 2011

(54) METHOD AND APPARATUS FOR MOLECULAR ANALYSIS USING NANOELECTRONIC CIRCUITS

(75) Inventors: Wei Wu, Mountain View, CA (US); Zhiyong Li, Palo Alto, CA (US); Shih-Yuan Wang, Palo Alto, CA (US); Philip J. Kuekes, Menlo Park, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 408 days.

This patent is subject to a terminal disclaimer.

(21) Appl. No.: 11/144,586

(22) Filed: Jun. 3, 2005

(65) Prior Publication Data

US 2006/0275778 A1 Dec. 7, 2006

(51) Int. Cl.
*C12M 1/00* (2006.01)
*G01N 15/06* (2006.01)
*C07H 21/04* (2006.01)

(52) U.S. Cl. ............... 435/283.1; 435/287.3; 435/288.4; 435/288.5; 422/68.1; 422/82.01; 422/82.02; 536/23.1

(58) Field of Classification Search .................. None
See application file for complete search history.

(56) References Cited

U.S. PATENT DOCUMENTS

| | | | |
|---|---|---|---|
| 6,627,067 B1 | 9/2003 | Branton et al. | |
| 6,699,667 B2 | 3/2004 | Keen | |
| 6,770,472 B2 | 8/2004 | Manalis et al. | |
| 6,773,926 B1 | 8/2004 | Freund et al. | |
| 6,818,964 B2 | 11/2004 | Surh et al. | |
| 7,129,554 B2 * | 10/2006 | Lieber et al. | 257/414 |
| 7,217,562 B2 * | 5/2007 | Cao et al. | 435/287.2 |
| 2002/0006632 A1 | 1/2002 | Ponnampalam et al. | |
| 2002/0150938 A1 | 10/2002 | Kneipp et al. | |
| 2002/0172963 A1 | 11/2002 | Kelley et al. | |
| 2003/0094953 A1 * | 5/2003 | Brooks et al. | 324/441 |
| 2003/0231531 A1 | 12/2003 | Baxter et al. | |
| 2003/0235922 A1 | 12/2003 | Olofsson et al. | |
| 2004/0132070 A1 | 7/2004 | Star et al. | |
| 2004/0157319 A1 | 8/2004 | Keen | |

(Continued)

FOREIGN PATENT DOCUMENTS

WO WO 0113432 A1 * 2/2001

OTHER PUBLICATIONS

Berman, David, et al., "Single-electron transistor as a charge sensor for semiconductor applications," J.Vac.Sci.Technol.B, vol. 15, No. 6, Nov./Dec. 1997, pp. 2844-2847.

(Continued)

*Primary Examiner* — Betty Forman

(57) ABSTRACT

Devices and methods for detecting the constituent parts of biological polymers are disclosed. A molecular analysis device comprises a molecule sensor and a molecule guide. The molecule sensor comprises a single electron transistor including a first terminal, a second terminal, and a nanogap or at least one quantum dot positioned between the first terminal and the second terminal. A nitrogenous material disposed on the at least one quantum dot is configured for an interaction with an identifiable configuration of a molecule. The molecule sensor develops an electronic effect responsive to the interaction. The molecule guide is configured for guiding at least a portion of the molecule substantially near the molecule sensor to enable the interaction.

38 Claims, 11 Drawing Sheets

U.S. PATENT DOCUMENTS

| | | | |
|---|---|---|---|
| 2004/0174521 A1 | 9/2004 | Drachev et al. | |
| 2004/0197843 A1 | 10/2004 | Chou et al. | |
| 2004/0209392 A1 | 10/2004 | Craighead et al. | |
| 2004/0219072 A1 | 11/2004 | Yamakawa et al. | |
| 2004/0262159 A1 | 12/2004 | Martin et al. | |
| 2006/0275779 A1* | 12/2006 | Li et al. | 435/6 |
| 2007/0063304 A1* | 3/2007 | Matsumoto et al. | 257/462 |
| 2007/0134667 A1* | 6/2007 | Ashley et al. | 435/6 |
| 2007/0178507 A1* | 8/2007 | Wu et al. | 435/6 |

OTHER PUBLICATIONS

Chen, Peng, et al., "Probing Single DNA Molecule Transport Using Fabricated Nanopores," Nano Lett., vol. 4, No. 11, 2004, pp. 2293-2298.

Goodnick, Stephen M., et al., "Quantum-Effect and Single-Electron Devices," IEEE Transactions on Nanotechnology, vol. 2, No. 4, Dec. 2003, pp. 368-385.

Guo, Lingjie, et al., "A room-temperature silicon single-electron metal-oxide-semiconductor memory with nanoscale floating-gate and ultranarrow channel." Appl. Phys. Lett., vol. 70, No. 7, Feb. 17, 1997, pp. 850-852.

Li, Z., et al., "Sequence-Specific Label-Free DNA Sensors Based on Silicon Nanowires," Nano Lett., vol. 4, No. 2, 2004, pp. 245-247.

Michaels, Amy M., et al., "Surface Enhanced Raman Spectroscopy of Individual Rhodamine 6G Molecules on Large Ag Nanocrystals," J. Am. Chem. Soc., vol. 121, No. 43, 1999, pp. 9932-9939.

Moore, Samuel K., ed., "Making Chips to Probe Genes," IEEE Spectrum, Mar. 2001, pp. 54-60.

Pantelides, Sokrates T., et al., "Molecular Electronics by the Numbers," IEEE Transactions on Nanotechnology, vol. 1, No. 1, Mar. 2002, pp. 86-90.

Sauer-Budge, Alexis F., et al., "Unzipping Kinetics of Double-Stranded DNA in a Nanopore," Physical Review Letters, vol. 90, No. 23, Jun. 13, 2003, pp. 238101-1 through 238101-4.

Song, Ki-Whan, et al., "Realistic Single-Electron Transistor Modeling and Novel CMOS/SET Hybrid Circuits," IEEE, 2003, pp. 119-121.

Van Den Brom, Helko E., et al., "Counting Electrons One by One—Overview of a Joint European Research Project," IEEE Transactions on Instrumentation and Measurement, vol. 52, No. 2, Apr. 2003, pp. 584-589.

Van Houten, H., et al., "Quantized Conductance of Point Contacts in a Two-Dimensional Electron Gas," Physical Review Letters, Vol. 60, No. 9, Feb. 29, 1988, pp. 848-850.

Wu, Wei, et al., "Room-temperature Si single-electron memory fabricated by nanoimprint lithography," Applied Physics Letters, vol. 83, No. 11, Sep. 15, 2003, pp. 2268-2270.

Wu, Wei, Thesis, 141 pages.

Yano, Kazuo, et al., "Room-Temperature Single-Electron Memory" IEEE Transactions on Electron Devices, vol. 41, No. 9, Sep. 1994, pp. 1628-1638.

Zhuang, Lei, et al., "Silicon single-electron quantom-dot transistor switch operating at room temperature," Appl. Phys. Lett., vol. 72, No. 10, Mar. 9, 1998, pp. 1205-1207.

Hahm, Jong-in, et al., "Direct Ultrasensitive Electrical Detection of DNA and DNA Sequence Variations Using Nanowire Nanosensors," Nano Lett., vol. 4, No. 1, pp. 51-54, 2004.

Wang, Wayne U., et al., "Label-free detection of small-molecule-protein interactions by using nanowire nanosensors," PNAS, vol. 102, No. 9, pp. 3208-3212, Mar. 1, 2005.

* cited by examiner

| AAA | AAT | AAG | AAC | ATA | ATT | ATG | ATC |
|-----|-----|-----|-----|-----|-----|-----|-----|
| AGA | AGT | AGG | AGC | ACA | ACT | ACG | ACC |
| TAA | TAT | TAG | AAC | TTA | TTT | TTG | TTC |
| TGA | TGT | TGG | AGC | TCA | TCT | TCG | TCC |
| GAA | GAT | GAG | GAC | GTA | GTT | GTG | GTC |
| GGA | GGT | GGG | GGC | GCA | GCT | GCG | GCC |
| CAA | CAT | CAG | CAC | CTA | CTT | CTG | CTC |
| GGA | CGT | CGG | CGC | CCA | CGT | CCG | CCC |

*FIG. 13*

METHOD AND APPARATUS FOR MOLECULAR ANALYSIS USING NANOELECTRONIC CIRCUITS

FIELD OF THE INVENTION

The present invention relates to chemical analysis using nanoelectronic circuits. More particularly, the present invention relates to systems for determining chemical sequences of biological polymers using nanoscale transport systems and single electron transistors.

BACKGROUND OF THE INVENTION

Determining the sequence of a Deoxyribonucleic acid (DNA) molecule is, conventionally, a difficult and expensive chemical process. However, with the rapid growth in nanotechnology, new methods may be devised to increase accuracy, speed, and cost of determining the constituent parts of biological polymers such as proteins, DNA, and ribonucleic acid (RNA).

Various methods have been developed for determining the chemical composition of portions of a DNA strand or the chemical composition of an entire DNA strand. One such method involves creating a micro-array with hundreds or thousands of patches of single stranded DNA, which are often referred to as probes, attached to various locations on a substrate such as glass or silicon.

When using this DNA detection method, the DNA to be examined is first transcribed into RNA. RNA is a chemical very similar to DNA that can encode the same information as DNA. The RNA can then be used to create single stranded DNA (ssDNA) copies of the RNA. Fluorescent molecules, also referred to as tags, are then bonded onto the new single stranded DNA molecules.

When these tagged single stranded DNA molecules are washed over the micro-array, they will bond and stick to any of the single stranded DNA probes having a gene sequence with bases that are complementary to, but arranged in the same order as, the bases of the tags. Then, a light source exposing the micro-array causes the tagged DNA molecules that have stuck to the micro-array to fluoresce. The fluorescent glow can be detected and, based on where the various DNA tags were placed and their corresponding sequence, the sequence of the portion of the DNA stuck to that site can be determined.

Unfortunately, this process requires a significant number of chemical and optical steps to determine various portions of a DNA sequence. In addition, the detection is limited to the variety of DNA probes on the micro-array. Long probes, with a large number of sequences can detect a significant match, but it becomes difficult to place every possible variation of long probes on a single micro-array. On the other hand, short probes may be incapable of detecting a desired long sequence.

Another proposed detection method involves examining a polymerase chain reaction replication process. An RNA polymerase may attach to a DNA molecule and begin separating the DNA strand. The RNA polymerase then traverses along the DNA strand opening newer regions of the DNA strand and synthesizing an RNA strand matching the opened portions of the DNA. As the RNA polymerase traverses along the DNA, the portion of the DNA opened by the RNA polymerase closes down and re-bonds after leaving the RNA polymerase. In this detection method, the RNA polymerase is attached to an electronic device, such as a single electron transistor. Whenever the polymerase replication takes place, a charge variation may occur on the single electron transistor for each portion of the DNA molecule opened up by the RNA polymerase. By detecting these charge variations, the composition of the portion of the DNA molecule that is transcribed can be determined.

Unfortunately, the polymerase chain reaction method relies on the occurrence of this biological process of replication. In addition, the RNA polymerase replication only begins and ends at certain defined points of the DNA strand. As a result, it may be difficult to discover all portions of the DNA strand to be examined.

A device and method with the flexibility to examine the entire sequence of a DNA strand, without requiring complicated chemical and optical processing, is needed. A molecule detection system using nanoelectronic devices without the requirement of a biological replication process may be a smaller and less costly system than conventional approaches. This integrated molecule detection system would be easier to use and may be adaptable to detect a variety of predetermined sets of bases within DNA molecules. Furthermore, this molecule detection system may be integrated with other electronic devices for further analysis and categorization of the detected molecules.

BRIEF SUMMARY OF THE INVENTION

The present invention, in a number of embodiments, includes molecular analysis devices and methods for detecting the constituent parts of biological polymers. An exemplary embodiment of a molecular analysis device comprises a molecule sensor and a molecule guide. The molecule sensor comprises a single electron transistor including a first terminal, a second terminal, and at least one quantum dot positioned between the first terminal and the second terminal. A nitrogenous material disposed on the at least one quantum dot is configured to interact with an identifiable configuration of a molecule. The molecule sensor develops an electronic effect responsive to the interaction. The molecule guide is configured for guiding at least a portion of the molecule substantially near the molecule sensor to enable the interaction.

Another exemplary embodiment of a molecular analysis device comprises a plurality of molecule sensors and a molecule guide. Each molecule sensor comprises a single electron transistor including a first terminal, a second terminal, and at least one quantum dot positioned between the first terminal and the second terminal. A nitrogenous material disposed on the at least one quantum dot of each of the plurality is configured to interact with an identifiable configuration of a molecule. Each molecule sensor develops an electronic effect responsive to the interaction. The molecule guide is configured for guiding at least a portion of the molecule substantially near the nitrogenous material of each of the plurality of molecule sensors to enable the interaction.

Another exemplary embodiment of a molecular analysis device comprises a molecule sensor and a molecule guide. The molecule sensor comprises a first terminal, a second terminal, and a nanogap located between the first terminal and the second terminal. A nitrogenous material disposed on the nanogap is configured to interact with an identifiable configuration of a molecule. The molecule sensor develops an electronic effect responsive to the interaction. The molecule guide is configured for guiding at least a portion of the molecule substantially near the molecule sensor to enable the interaction.

Another exemplary embodiment includes a method of detecting a molecule. The method includes guiding at least a portion of the molecule substantially near a molecule sensor.

The molecule sensor includes at least one quantum dot disposed between a first terminal and a second terminal. The method further includes developing an interaction between an identifiable configuration of the molecule and a nitrogenous material, which is disposed on the at least one quantum dot. The method further includes sensing an electronic effect in the molecule sensor responsive to the interaction.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

FIG. 13 is a top view of an exemplary embodiment of a molecular analysis device including a large number of molecule sensors configured to detect a variety of molecule configurations.

DETAILED DESCRIPTION OF THE INVENTION

Figure 1A:
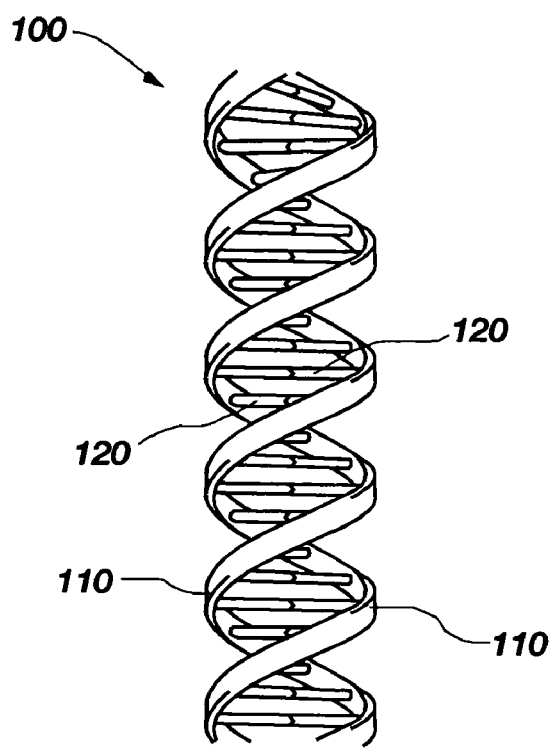
FIG. 1A is a three dimensional view of a portion of a DNA molecule.
Figure 1B:
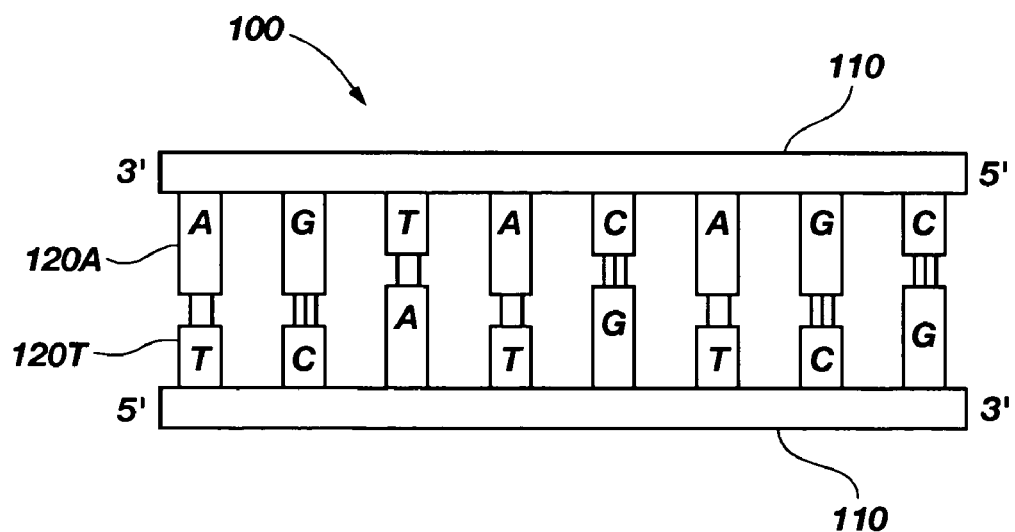
FIG. 1B is a flat view of a portion of a DNA molecule showing various possible base pair bondings.

The present invention, in a number of embodiments, includes structures, devices, and methods for use in detecting the molecular structure of biological polymers. As illustrated in FIGS. 1A and 1B, an example of one such biological polymer is Deoxyribonucleic acid (DNA). A DNA molecule 100 comprises a double helix structure including two backbone strands 110 on the outside of the double helix. The backbone strands 110 are a structure made up of sugar-phosphate polymer strands. Between the two backbone strands 110 are pairs of bases 120 configured similar to ladder rungs. The bases 120 connecting the strands consist of four types: adenine 120A (A), thymine 120T (T), guanine 120G (G), and cytosine 120C (C). RNA, which is closely related to DNA, comprises a similar structure including the A, G, and C bases of DNA. However, in RNA, rather than bonding with T, A bonds with the molecule uracil (U) (not shown), which is closely related to T. In addition, while RNA can form a double helix, in nature it generally exists as a single strand.

Each of the base molecules 120 comprise nitrogenous compounds in various configurations. The base molecules 120 may bond with each other to form base pairs. As shown in FIG. 1B, T may form two weak hydrogen bonds with A, while C may form three weak hydrogen bonds with G. These weak bonds between the base pairs allow a DNA strand to be separated into two complementary single stranded molecules. A single human DNA molecule may include as many as three billion of these base pairs.

Another way of characterizing the constituent parts of a DNA strand is to consider the various bases 120 chemically bonded to a sugar. In this form, the resultant molecule is often referred to as a nucleoside. Each nucleoside includes a sugar molecule bonded to one of the various bases 120. A nucleoside with a phosphate molecule bonded to the sugar portion of the nucleoside is often referred to as a nucleotide. Thus, each strand of a DNA molecule may be considered as a plurality of nucleotides bonded together, wherein the bonds form at the sugar-phosphate portion of each nucleotide to form the backbone 110 of the strand. Nucleotides join together to form the backbone strands 110 by a 5'-3' phosphodiester linkage, giving the strands a directionality. Thus, the 5' end of the strand has a free phosphate group and the 3' end has a free hydroxyl group. In double stranded DNA, the backbone strands 110 run in opposite directions such that each end of the double strand has a 5' end on one backbone strand 110 and a 3' end on the other backbone strand 110.

A section of single stranded DNA including a small plurality of nucleotides is often referred to as an oligonucleotide. These oligonucleotides are conventionally used as the tags in the prior art DNA micro-arrays previously described.

In genetic coding, an oligonucleotide comprising three consecutive nucleotides along RNA or single stranded DNA is often referred to as a codon. Any three consecutive nucleotides of A, C, G, and T (or U for RNA), can be combined in 64 (i.e., $4^3$) possible combinations. The 20 different amino acids are specified by these 64 different codons and are represented by more than one codon. For example, the amino acid Alanine may be represented by the codons GCA, GCC, GCG, and GCU.

Polypeptides and proteins (one or more polypeptide chains) are composed of a linear chain of amino acids covalently linked by peptide bonds. In addition to the codons that specify the various amino acids, some codons are defined as start codons and stop codons. These start and stop codons define the beginning and ending of the sequence of amino acids to be formed that ultimately form any given polypeptide or protein. Thus, identification of the various amino acids by direct identification of the 64 possible codons is possible.

Figure 2A:
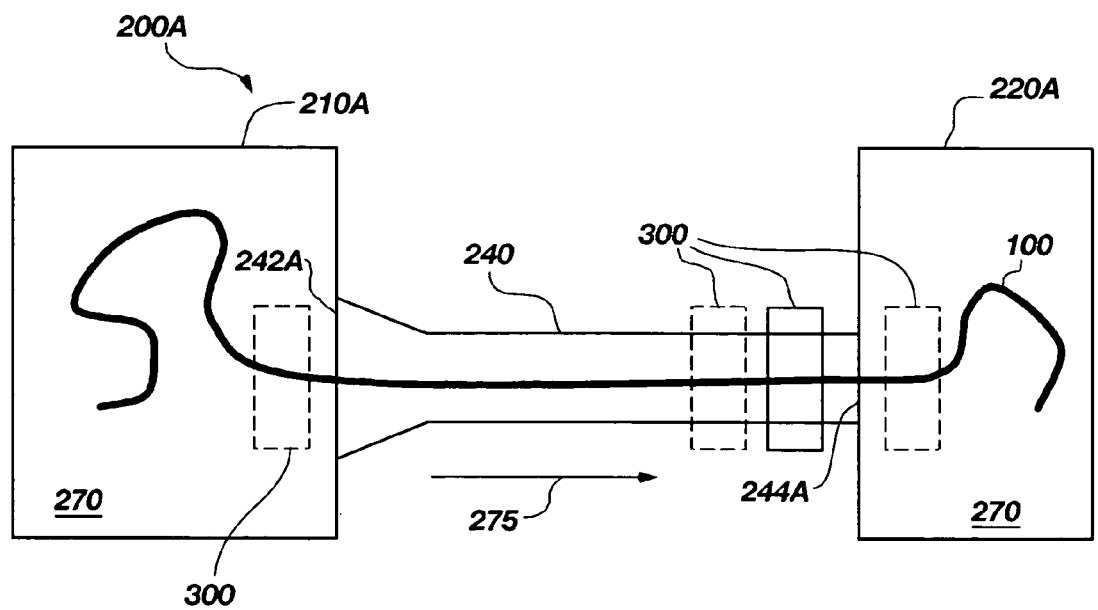
FIG. 2A is a top view of an exemplary molecular analysis device including a nanochannel and one or more molecule sensors disposed in the nanochannel and substantially near the nanochannel.

FIG. 2A illustrates an exemplary embodiment of a molecular analysis device 200A for analyzing biological polymers such as nucleic acid chains, including DNA and RNA. The molecular analysis device 200A includes a supply reservoir 210A, an accumulation reservoir 220A, a molecule guide (such as a nanochannel 240 shown in FIG. 2A), and at least one molecule sensor 300. In addition, a transport medium 270, such as, for example, an electrolyte solution, may be contained within the supply reservoir 210A, the nanochannel 240, and the accumulation reservoir 220A. At least one nucleic acid chain 100 may be disposed within the transport medium 270. The molecule sensor 300 is described in more detail below.

The nanochannel 240 may be configured as a nanofluidic channel for carrying the nucleic acid chain 100 in the transport medium 270 from the supply reservoir 210A, through the nanochannel 240, to the accumulation reservoir 220A in the transport direction 275 shown. Alternatively, the transport medium 270 may be configured for carrying the nucleic acid chain 100 from the accumulation reservoir 220A, through the nanochannel 240 to the supply reservoir 210A. Various methods may be used to transport the nucleic acid chain 100 through the nanochannel 240, such as, by way of example, electrokinetic flow, electroosmotic flow, hydrostatic pressure, hydrodynamic pressure, and hydromagnetic flow. These transport mechanisms may be caused by mechanical, magnetic, electrical field, heat-induced, and other methods known to a person of ordinary skill in the art.

Electrophoresis causes the movement of particles that are suspended in a medium to which an electromotive force is applied. Particularly, a particle or molecule having an electrical charge will experience an electromotive force when positioned within an electrical field. Nucleic acid chains 100 are good candidates for electrophoresis because they carry multiple negative charges due to the phosphate group and the phosphodiester backbone strand 110 (FIGS. 1A and 1B). Thus, when electrodes (not shown) with a voltage differential are placed in the transport medium 270, the nucleic acid chains 100 will migrate toward the more positive electrode. By way of example, if an electrode with a ground potential is placed in the supply reservoir 210A and an electrode with a positive voltage is placed in the accumulation reservoir 220A, nucleic acid chains 100 in the transport medium 270 will migrate from the supply reservoir 210A, through the nanochannel 240, and toward the electrode in the accumulation reservoir 220A. Furthermore, the movement rate or velocity of the nucleic acid chain 100 substantially correlates with the voltage bias between the electrodes. As a result, a first approximation of the nucleic acid chain 100 velocity may be determined, which may be used by, and refined by, signal processing analysis in combination with signal data from the molecule sensor 300 to determine the constituent parts of the nucleic acid chain 100.

Other transport mechanisms may rely on nanofluidic flow of the transport medium 270 itself, with the nucleic acid chain 100 being carried along with the transport medium 270. For example, electrokinetic flow (often referred to as electroosmotic flow) is generated in a similar manner to electrophoresis by electrodes (not shown) in the supply reservoir 210A and the accumulation reservoir 220A. Electrokinetic flow of the transport medium 270 may generally require higher voltage potentials to cause transport medium 270 flow than the voltage required to cause electrophoretic movement of the nucleic acid chains 100. Thus, nucleic acid chain 100 movement may be substantially electrophoretic or may be a combination of electrophoretic movement and movement caused by electrokinetic flow of the transport medium 270.

Yet another transport mechanism may rely on pressure driven flow. In very small channels, such as nanochannels 240, a small pressure differential may be developed by applying a temperature differential between the supply reservoir 210A and the accumulation reservoir 220A. This small pressure differential may cause the flow of the transport medium 270, and nucleic acid chains 100 within the transport medium 270, from one reservoir (210A, 220A) to the other reservoir (220A, 210A).

Figure 3A:
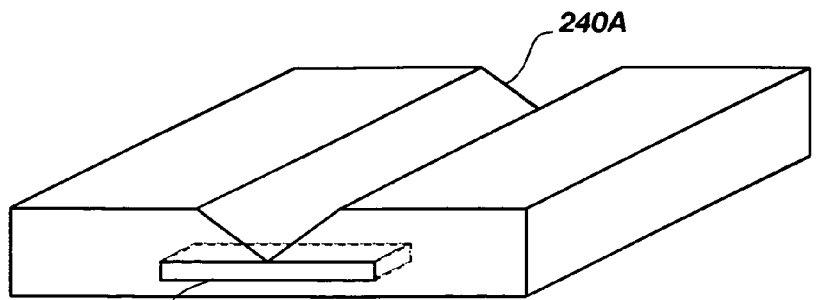
FIGS. 3A, 3B, 3C, and 3D are three dimensional views of exemplary configurations of nanochannels useful in practicing the present invention.
Figure 3B:
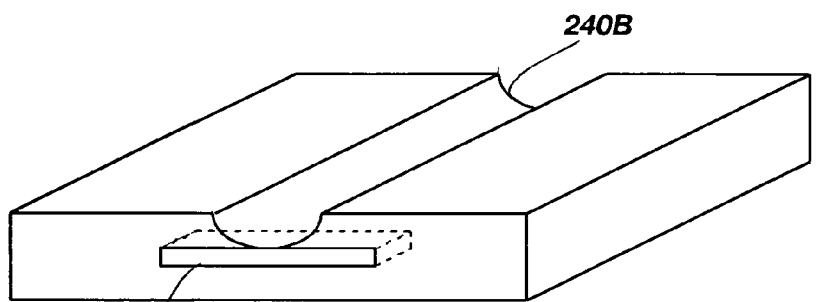
Figure 3C:
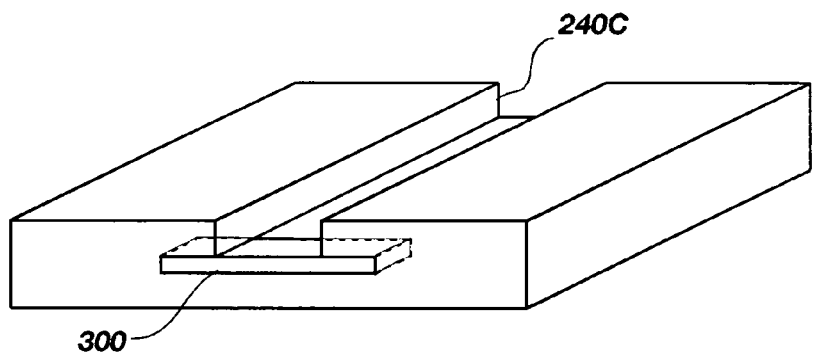
Figure 3D:
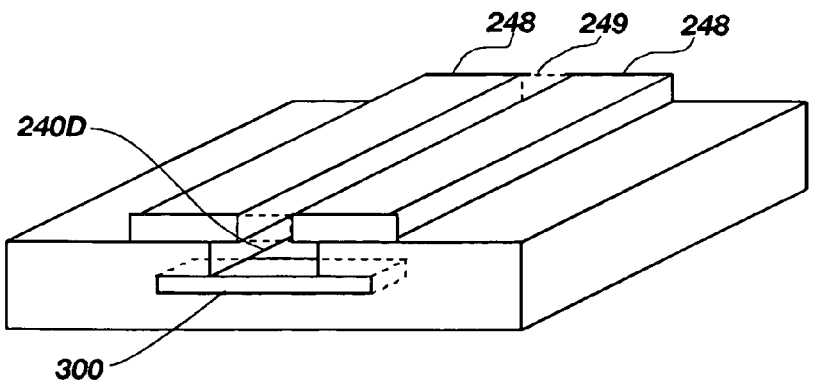

As shown in FIGS. 3A through 3D, the nanochannel 240 may be formed in a variety of configurations and cross sections. FIG. 3A illustrates a nanochannel 240A with a triangular cross section and a molecule sensor 300 positioned in the nanochannel 240A. FIG. 3B illustrates a nanochannel 240B with a semi-elliptical cross section and a molecule sensor 300 positioned in the nanochannel 240B. FIG. 3C illustrates a nanochannel 240C with a rectangular cross section and a molecule sensor 300 positioned in the nanochannel 240C. FIG. 3D illustrates a nanochannel 240D with a rectangular cross section and a molecule sensor 300 positioned in the nanochannel 240D. FIG. 3D further illustrates a partial channel cover 248 formed over a portion of the nanochannel 240 so that the nanochannel 240 is partially enclosed. Alternatively, a full channel cover 249 may be formed over the entire nanochannel 240 as shown by the dashed lines indicating a fully enclosed nanochannel 240.

Other nanochannel 240 cross sections are contemplated as being within the scope of the present invention, such as, by way of example and not limitation, circular, semi-circular, triangular, square, and hexagonal. Of course, the partially enclosed and fully enclosed nanochannel embodiments shown in FIG. 3D may be used with any of the various cross sections.

The nanochannels 240, partial channel covers 248, and full channel covers 249 may be fabricated using a variety of lithographic techniques, nano-imprint lithographic techniques, self-assembly techniques, template synthesis, wafer bonding, or combinations thereof. Additionally, the nanochannel 240 may be formed initially as a fully enclosed structure without the need for additional steps to form a partial channel cover 248 or full channel cover 249.

The length of the nanochannel 240 may vary from nanometers to orders of magnitude longer for adaptation to various applications and nucleic acid chain 100 lengths to be analyzed. Furthermore, the nanochannels 240 may include curves of a radius favorable to nucleic acid chain 100 flow and may be configured to enable long channels in a restricted area.

The nanochannel 240 is configured to at least partially straighten the nucleic acid chain 100 such that loops do not form within the channel and such that the nucleic acid chain 100 may be presented substantially near the molecule sensor 300. To ensure that loops do not form within the channel, in a particular embodiment, the channel cross section may need to be about twice the persistence length of the nucleic acid chain 100, or less. At room temperature, the persistence length for double stranded DNA is about 50 nm (i.e., L). Therefore, the nanochannel 240 should be about 100 nm (i.e., 2 L) or less to ensure that loops do not form.

To ensure that the nucleic acid chain 100 is presented substantially near the molecule sensor 300, the nanochannel 240 may need to be significantly narrower than the width needed to keep the nucleic acid chain 100 from forming loops. Thus, nanochannel 240 cross section dimensions may vary depending on the type of molecule sensor 300 used, as explained more fully below in the discussion of the molecule sensor 300. Furthermore, the cross section dimensions may vary along the length of the nanochannel 240. For example, a nanochannel 240 may have a relatively wide cross section for much of its length and narrow down to a smaller cross section near a molecule sensor 300.

Returning to FIG. 2A, a molecule sensor 300 is shown in the nanochannel 240 near an exit point 244A of the nanochannel 240. Other optional molecule sensors 300 are also shown to illustrate the flexibility and possibilities for positioning of the molecule sensors 300 relative to the nanochannel 240 and nucleic acid chain 100. It may be desirable to place multiple molecule sensors 300 in various positions to detect various portions of the nucleic acid chain 100. For example, an optional molecule sensor 300 is shown in the nanochannel 240, an optional molecule sensor 300 is shown in the supply reservoir 210A substantially near an entrance point 242A of the nanochannel 240, and an optional molecule sensor 300 is shown in the accumulation reservoir 220A substantially near the exit point 244A of the nanochannel 240. Molecule sensors 300 outside of the nanochannel 240 (i.e., near the entrance point 242A or exit point 244A) may be placed in a location where the nucleic acid chain 100 is still presented substantially near the molecule sensors 300 and where the nucleic acid chain 100 has not assumed an un-straightened configuration. It will be understood by those of ordinary skill in the art that the labeling of entrance point 242A and exit point 244A are arbitrary, as the molecular analysis device 200A may be configured to cause flow of the nucleic acid chain 100 in either direction through the nanochannel 240.

Figure 2B:
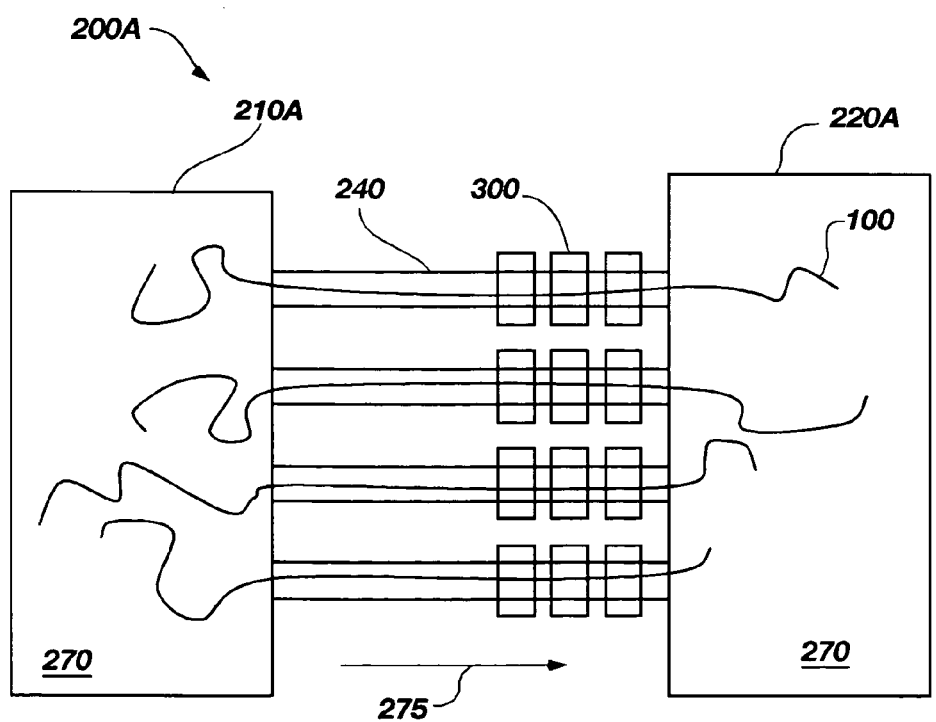
FIG. 2B is a top view of an exemplary molecular analysis device including a plurality of nanochannels and molecule sensors disposed in the nanochannel.

FIG. 2B illustrates a plurality of nanochannels 240 all coupled to a single supply reservoir 210A and a single accumulation reservoir 220A, with a nucleic acid chain 100 in each of the plurality of nanochannel 240. In addition, each of the nanochannels 240 is shown with a plurality of molecule sensors 300 in the nanochannels 240 and a transport direction 275 from the supply reservoir 210A to the accumulation reservoir 220A. A person of ordinary skill in the art will appreciate that many configurations of reservoirs (210A, 220A), nanochannels 240, and molecule sensors 300 are contemplated within the scope of the invention.

Figure 4A:
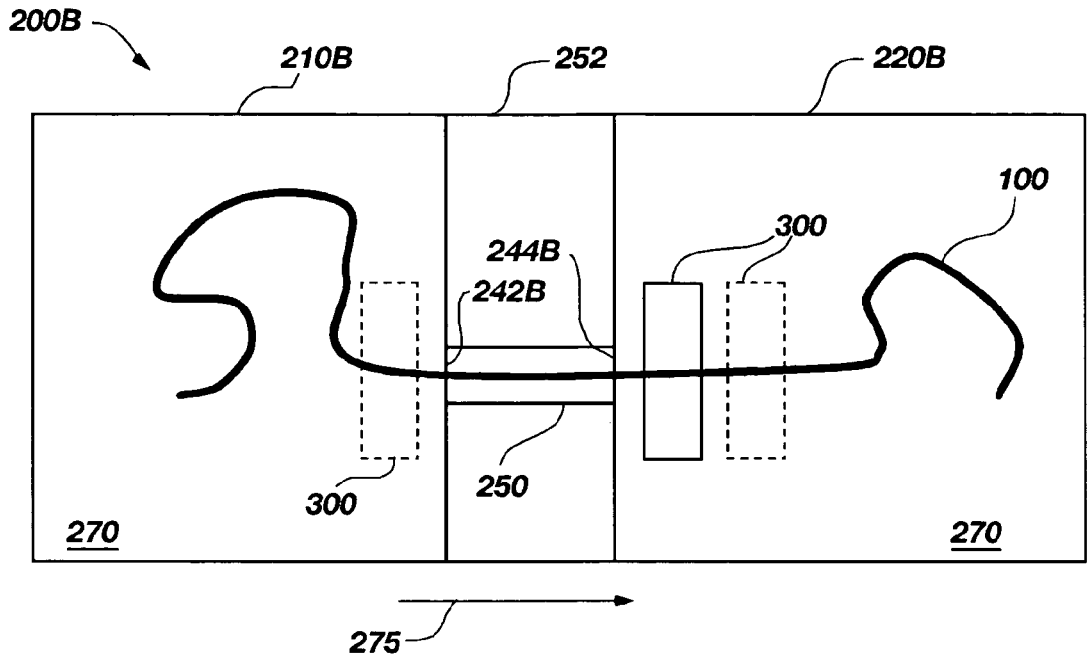
FIG. 4A is a top view of an exemplary molecular analysis device including a nanopore and one or more molecule sensors.

FIG. 4A illustrates another exemplary embodiment of a molecular analysis device 200B for analyzing biological polymers. The molecular analysis device 200B includes a supply reservoir 210B, an accumulation reservoir 220B, a molecule guide (also referred to as a nanopore 250 in the embodiment of FIG. 4A), and a molecule sensor 300. In addition, a transport medium 270, such as, for example, an electrolyte solution, may be contained within the supply reservoir 210B, the nanopore 250, and the accumulation reservoir 220B. At least one nucleic acid chain 100 may be disposed within the transport medium 270. The molecule sensor 300 is described in more detail below.

The nanopore 250 may be configured for carrying the nucleic acid chain 100 in the transport medium 270 from the supply reservoir 210B, through the nanopore 250, to the accumulation reservoir 220B in the transport direction 275 shown. Alternatively, the transport medium 270 may be configured for carrying the nucleic acid chain 100 from the accumulation reservoir 220B, through the nanopore 250, to the supply reservoir 210B. The same methods discussed above for transportation of the nucleic acid chain 100 through the nanochannel 240 of FIGS. 1 and 2 are applicable for transportation of the nucleic acid chain 100 through the nanopore 250.

Figure 4B:
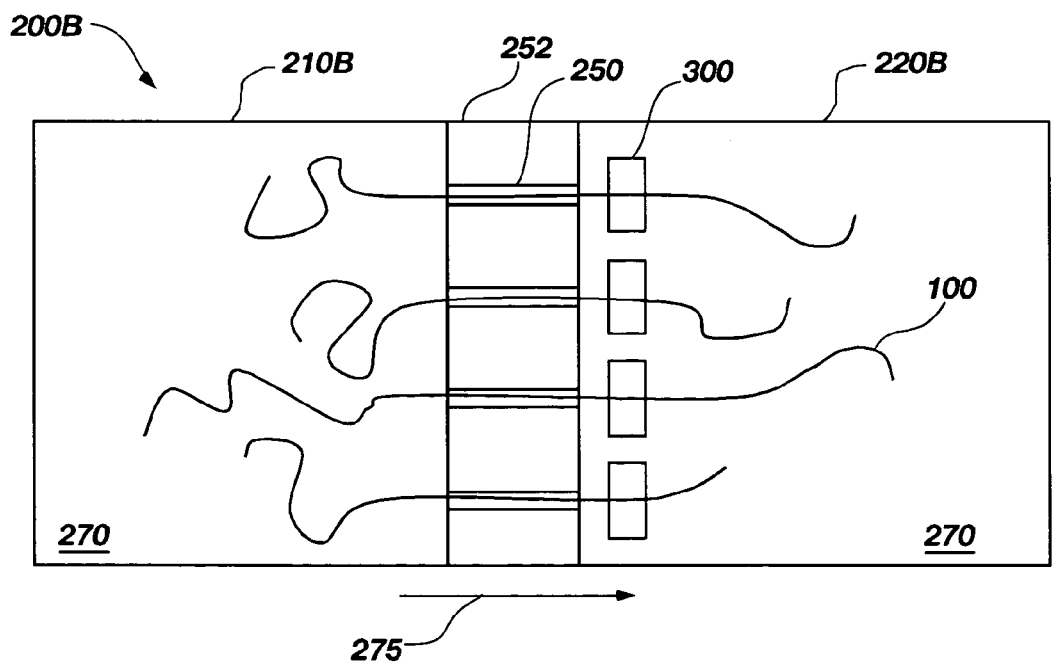
FIG. 4B is a top view of an exemplary molecular analysis device including a plurality of nanopores and a plurality of molecule sensors.
Figure 4C:
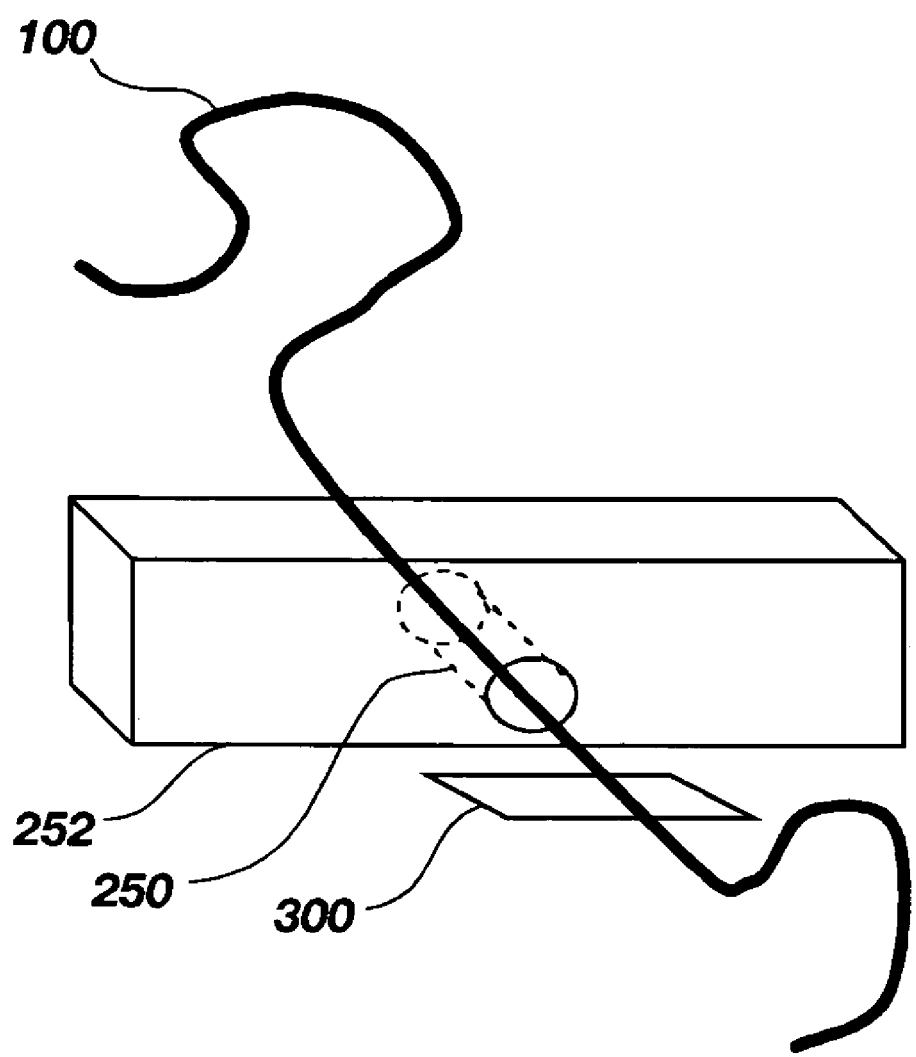
FIG. 4C is a three dimensional view of an exemplary configuration of a nanopore and a molecule sensor.

A nanopore 250, as shown in FIGS. 4A, 4B, and 4C has an opening of from about 1 nanometer to about 100 nanometers, in a membrane 252. The membrane 252 may comprise an organic or inorganic material, which may be fabricated using a variety of lithographic techniques, nano-imprint lithographic techniques, self-assembly techniques, template synthesis, wafer bonding, or combinations thereof.

The nanopore 250 may be cylindrical in shape (as shown in FIG. 4C) or may include other cross sectional shapes such as, by way of example only, triangular, square, hexagonal, and octagonal. The figures illustrating nanopores 250 in membranes 252 are generally shown with a nanopore 250 configured horizontally through a vertical membrane 252. However, the membrane 252 may be disposed horizontally, with a vertical nanopore 250 therethrough, or any other suitable configuration, so long as the nanopore 250 may be configured to present successive segments of the nucleic acid chain 100 substantially near the molecule sensor 300, as explained below.

In a particular embodiment, the nanopore 250 may be about 100 nm or less to ensure the nucleic acid chain 100 does not pass through the nanopore 250 in some type of looped configuration, as explained above in the discussion of persistence length. To ensure that the nucleic acid chain 100 is presented substantially near the molecule sensor 300, the nanopore 250 may need to be significantly narrower than the width needed to keep the nucleic acid chain 100 from forming loops. Thus, nanochannel 240 cross section dimensions may vary depending on the type of molecule sensor 300 used, as explained more fully below in the discussion of the molecule sensor 300.

The membrane 252 may be a wide variety of thicknesses because the invention uses the nanopore 250 as a presentation and transport mechanism, rather than a sensing mechanism. A relatively thin membrane 252 may enable more uniform nanopores 250. A relatively thick membrane 252 may assist in straightening the nucleic acid chain 100 in the vicinities of the nanopore 250 entrance point 242B and nanopore 250 exit point 244B, allowing additional molecule sensors 300 to be lined up in the area where the nucleic acid chain 100 remains relatively straight such that it can be transported substantially close to a plurality of molecule sensors 300.

In FIG. 4A, a molecule sensor 300 is shown substantially near an exit point 244B of the nanopore 250. Other optional molecule sensors 300 are also shown to illustrate the flexibility and possibilities for positioning of the molecule sensors 300 relative to the nanopore 250 and nucleic acid chain 100. It may be desirable to place multiple molecule sensors 300 in positions to detect various portions of the nucleic acid chain 100. As examples, an optional molecule sensor 300 is shown in the supply reservoir 210B substantially near an entrance point 242B of the nanopore 250, and an additional molecule sensor 300 is shown in the accumulation reservoir 220B near the exit point 244B of the nanopore 250. Molecule sensors 300 near the entrance point 242B or exit point 244B may be placed in a location where the nucleic acid chain 100 is presented substantially near the molecule and wherein the nucleic acid chain 100 has not assumed its folded (un-straightened) configuration. It will be understood by those of ordinary skill in the art that the labeling of entrance point 242B and exit point 244B are arbitrary, as the molecular analysis device 200 may be configured to cause flow of the nucleic acid chain 100 in either direction through the nanopore 250.

FIG. 4B illustrates a plurality of nanopores 250 all coupled to a single supply reservoir 210A and a single accumulation reservoir 220B, with a nucleic acid chain 100 in each of the plurality of nanopores 250 and a transport direction 275 from the supply reservoir 210B to the accumulation reservoir 220B. A person of ordinary skill in the art will appreciate that many configurations of reservoirs (210B, 220B), nanopores 250, and molecule sensors 300 are contemplated within the scope of the invention.

Figure 5:
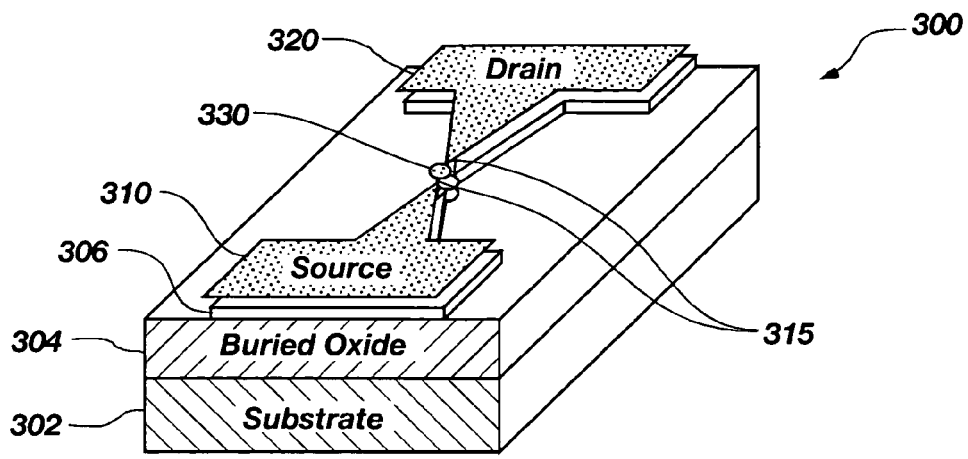
FIG. 5 is a three dimensional view of an exemplary embodiment of a molecule sensor comprising an exemplary single electron transistor.

FIG. 5 illustrates an exemplary molecule sensor 300 configured as a single electron transistor (SET). The SET 300 includes a source 310 (also referred to as a first terminal), and a drain 320 (also referred to as a second terminal). Positioned between the source 310 and drain 320, is a quantum dot 330 embedded in a tunneling layer 306. Exemplary tunneling layers are silicon dioxide or other suitable dielectric. The dielectric forms tunneling junctions 315. One tunneling junction 315 operably couples the source 310 to the quantum dot 330, and another tunneling junction 315 operably couples the drain 320 to the quantum dot 330. The exemplary molecule sensor 300 may be formed on a silicon substrate 302 with a buried oxide layer 304 formed thereon. The SET also includes a third terminal configured for biasing an electronic effect of the SET. The third terminal (also referred to as a gate) may be configured as a side gate 340 (shown in FIGS. 8A and 8B) positioned to the side of and substantially in the same plane as the quantum dot. The gate may also be configured as a top gate (not shown) positioned above the quantum dot or as a back gate, wherein the substrate 302 (shown in FIG. 5) below the quantum dot acts as a gate.

A SET operates in many ways similar to a field effect transistor (FET), except that in a conventional conducting FET, thousands or millions of electrons may traverse from the source 310 to the drain 320. In a SET 300, as few as one electron at a time may leave the source 310 node or arrive at the drain 320 node.

A SET 300 may include two primary phenomena: a single electron effect and a quantum effect. Until the feature sizes of the SET 300 become extremely small (e.g., less than 5 nm for a quantum dot 330 embedded in $SiO_2$), the single electron effect dominates. In understanding the single electron effect, the quantum dot 330 may be considered like a capacitor. The electrostatic energy stored in a capacitor with a charge of q is given by:

$$E = \frac{q^2}{2C}$$

If the capacitance is small enough, the electrostatic energy of one electron may be larger than the thermal energy as represented by:

$$\frac{e^2}{2C} \geq k_B T$$

where e represents the charge of one electron and $k_b$ represent the Boltzman constant, and T is the temperature. If the electrostatic energy of one electron is larger than the thermal energy, the energy stored in the capacitor does not change continuously, and the charge and discharge of one electron onto the capacitor leads to an observable change in total energy.

For example, assume there are n electrons stored in the capacitor and one more electron (i.e. an n+1 electron) is to be charged onto the capacitor. The total electrostatic energy of the capacitor before the n+1 electron is charged is:

$$E_n = \frac{n^2 e^2}{2C}$$

Similarly, the total electrostatic energy of the capacitor after the n+1 electron is charged is:

$$E_{n+1} = \frac{(n+1)^2 e^2}{2C}$$

Therefore, the energy needed to charge the N+1 electron is:

$$\Delta E = E_{n+1} - E_n = \frac{(n+1)^2 e^2}{2C} - \frac{n^2 e^2}{2C} = \left(n + \frac{1}{2}\right)\frac{e^2}{C}$$

The electrostatic energy levels in the capacitor comprise discrete energy levels where the lowest energy level is $\in_0 = e^2/2C$ and the energy between each subsequent level is described as $\Delta \in = e^2/C$.

As noted, to observe these single-electron effects, the energy spacing between each discrete energy level must be larger than the thermal energy. For example, for a quantum dot 330 embedded in $SiO_2$, the quantum dot 330 will typically have a diameter of about 10 nm or less for the energy level spacing to be about three times larger than the thermal energy at room temperature.

If the quantum dot 330 is small enough to make the gap between each energy level larger than the thermal energy, then the energy inside the dot has a discrete spectrum. Tunneling of electrons from the source 310 to the quantum dot 330 or from the quantum dot 330 to the drain 320, via the tunneling junctions 315 is inhibited until the energy gap is overcome through an applied bias between the source 310 and drain 320. In other words, electrons only transfer from the source 310 to the quantum dot 330, one by one. This phenomenon is known as a Coulomb blockade.

Clear Coulomb blockade effects may be observed when the tunneling resistance between the quantum dot 330 and other terminals is larger than about 26 kOhms. This tunneling resistance, at which Coulomb blockade effects are seen, is often referred to as the "quantum resistance."

The SET 300 exhibits low conductance between source 310 and drain 320, inhibiting electron transfer, when the energy levels of the source 310 and drain 320 misalign with the energy level of the quantum dot 330. Conversely, when the energy levels of the source 310 and drain 320 align with the energy level of the quantum dot 330, the SET 300 exhibits high conductance, enabling electron transfer. This electronic effect 375 is shown in FIGS. 6 and 7.

Figure 6:
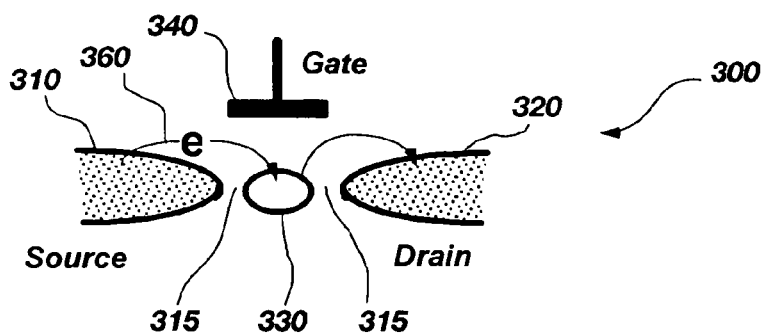
FIG. 6 is a schematic view of an exemplary single electron transistor.

An electrode configured as a gate 340 (also referred to as a third terminal), as shown in FIG. 6, may be placed close enough to the quantum dot 330 to affect the amount of energy needed to change the number of electrons on the quantum dot 330. For example, assume the bias voltage between the source 310 and drain 320 is held at a level below the Coulomb blockade voltage. As voltage on the gate 340 is increased, the energy level on the quantum dot 330 near the tunneling junctions 315 changes. At a certain point, the energy level of the source 310 and drain 320 will align with the energy level of the quantum dot 330 near the tunneling junction 315 and a new electron may be added to the quantum dot 330. When the electron is added, the SET 300 returns to a Coulomb blockade because the new energy level of the quantum dot 330 no longer aligns with the energy level of the source 310 and drain 320. Thus, for more electrons to move, the bias between the source 310 and drain 320 must change, or the gate 340 voltage must change, to overcome the Coulomb blockade. This makes the SET 300 very sensitive to charge changes on the gate 340, or other charges substantially near the quantum dot 330.

Figure 7:
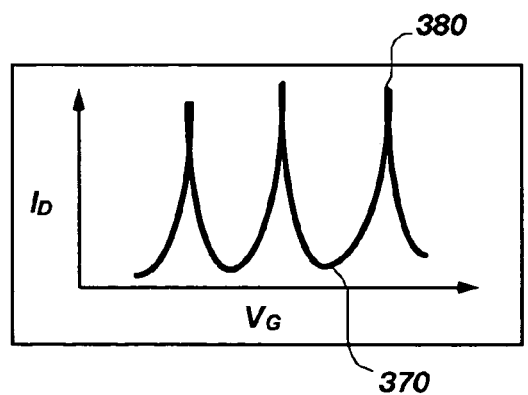
FIG. 7 is a graphical view of an electrical characteristic of an exemplary single electron transistor.

FIG. 7 illustrates the Coulomb blockade effect as a gate voltage versus drain current at a fixed source to drain bias level. The gate voltage is shown on the x-axis and the drain current is shown on the y-axis. As explained earlier, as the gate voltage increases, the SET 300 will reach a high conductance state 380, enabling electrons to transfer. However, a further increase will place the SET 300 in a low conductance state 370 inhibiting electron transfers 360.

One reason a SET 300 is useful for analysis of nucleic acid chains 100 is the charge sensitivity of a SET 300. A charge does not need to be in the quantum dot 330, it just needs to be close enough to influence the energy level of the quantum dot 330. This is often referred to as the Debye length, which is usually about 70 nm for lightly doped silicon. Heavy doping may reduce the Debye length. Thus, when a charged molecule is within the Debye length, the SET 300 will be able to detect the charge.

This Debye length also helps with noise rejection because the SET 300 is not influenced by a charge farther away than the Debye length. However, the Debye length also means that the nanochannel 240, nanopore 250, adjustment electrodes 340 (shown in FIGS. 8A and 8B, and explained below), or combinations thereof, must bring the nucleic acid chain 100 close enough to the quantum dot 330 to sense the intrinsic charge of the nucleic acid chain 100 at the location substantially near the quantum dot 330.

Figure 8A:
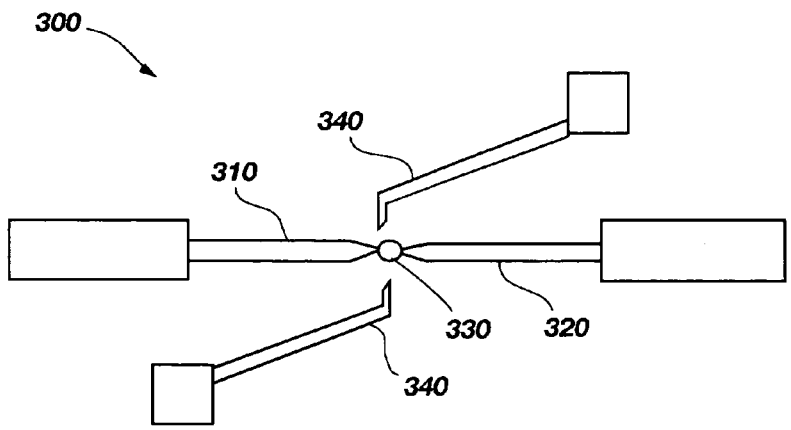
FIG. 8A is a top view of an exemplary single electron transistor including control electrodes.
Figure 8B:
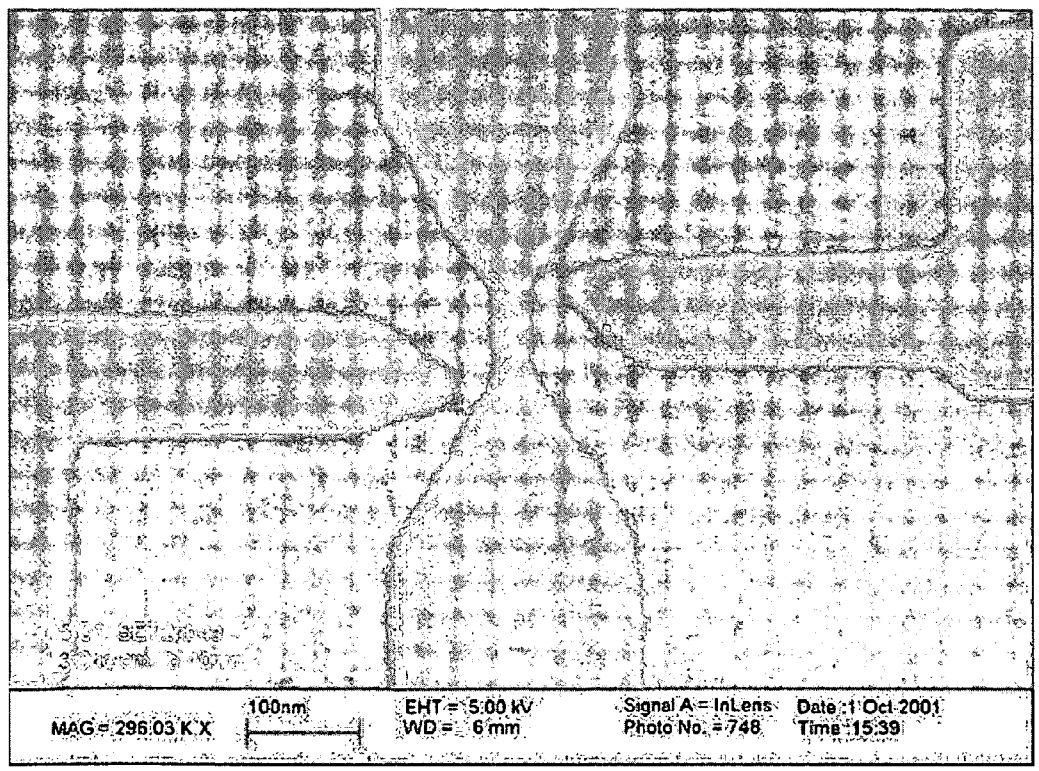
FIG. 8B is a scanning electron microscope picture of the exemplary single electron transistor of FIG. 8A.

FIG. 8A illustrates a SET 300, including the source 310, drain, and quantum dot 330. FIG. 8B is a scanning electron microscope picture (rotated 90 degrees counter-clockwise) of the exemplary single electron transistor of FIG. 8A. The FIG. 8A embodiment of the SET 300 also includes two electrodes 340 near the quantum dot 330. The electrodes 340 may be used as gates to the SET 300 to influence the Coulomb blockade level. The electrodes 340 may also perform an additional function. Because a nucleic acid chain 100 is negatively charged, the voltage of the electrodes 340 may be adjusted to cause the nucleic acid chain 100 to move forward or backward relative to the quantum dot 330. This may be thought of as a way to "fine-tune" the movement of the nucleic acid chain 100, which is caused by the electrophoresis or other transport mechanism described above. This fine-tuning also may be used to achieve a better alignment of the nucleic acid chain 100 relative to the quantum dot 330.

While not shown in the figures, another embodiment of the SET 300 may include a single electrode 340. However, two electrodes 340, one on each side of the quantum dot 330 may give additional control, enabling controllable movement of the nucleic acid chain 100 in both directions relative to the quantum dot 330. In yet another embodiment of the SET 300 (not shown), the gate 340 may be formed over the quantum dot 330, creating a gap between the quantum dot 330 and the gate 340 through which the transport medium 270 and the nucleic acid chain 100 may pass.

In addition, the discussion has focused on a silicon quantum dot implementation of a SET. However, other SET implementations are contemplated within the scope of the invention. For example, SETs may be formed using metal as the quantum dot. Typically, these SETs use an aluminum quantum dot, with aluminum oxide to form the tunneling junctions. As another example, SETs may be formed on III-V materials, such as GaAs, using metal gates to define a potential well for creation of a quantum dot. These SETs would usually have application at low temperatures due to the large quantum dot size, which requires a low thermal energy.

Figure 9:
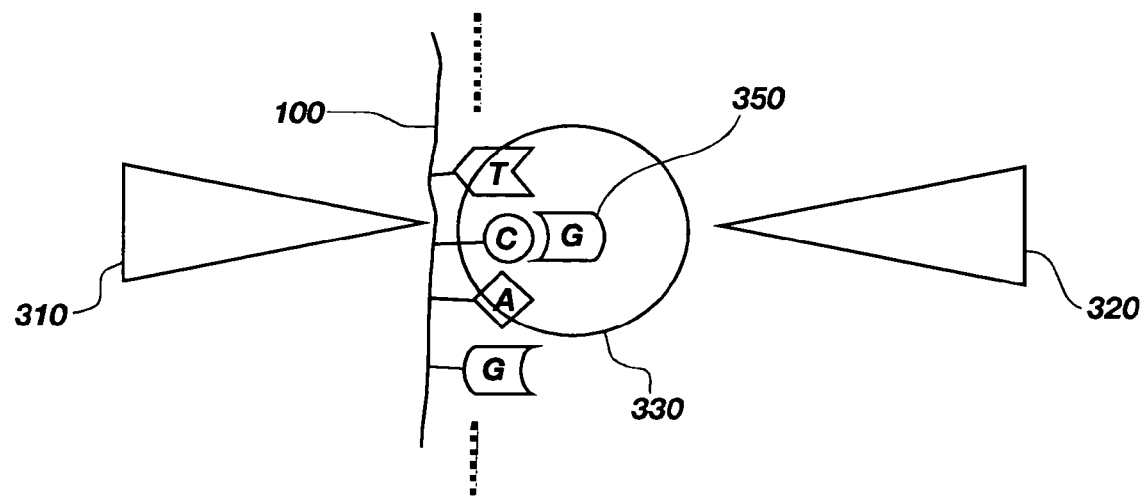
FIG. 9 is a top view of an exemplary single electron transistor including a nitrogenous material disposed on a quantum dot and an exemplary bonding to a nucleic acid chain.

FIG. 9 illustrates the source 310, drain 320, and quantum dot 330 of an exemplary SET 300. The quantum dot 330 in this exemplary SET 300 may be coated with a nitrogenous material 350. For example, for detecting portions of a nucleic acid chain 100, the nitrogenous material 350 may comprise a base selected from the group consisting of adenine 120A, thymine 120T, uracil 120U, cytosine 120C, and guanine 120G. Furthermore, the nitrogenous material 350 coating the quantum dot 330 may also include a sugar bonded to the base or a sugar-phosphate bonded to the base. By way of example, FIG. 9 illustrates the nitrogenous material 350 guanine (120G of FIG. 1B). FIG. 9 illustrates a representative symbol for the guanine 120G to show functional interaction with the nucleic acid chain 100. However, generally, the entire quantum dot 330 may be coated with the nitrogenous material 350.

As the nucleic acid chain 100 passes substantially near the coated quantum dot 330, a base 120 (in this example, C) of the nucleic acid chain 100 that is complementary to the nitrogenous material 350 (in this example, G) on the quantum dot 330 may react with the nitrogenous material 350. This reaction may take the form of a transitory chemical bond between the complementary base on the nucleic acid chain 100 and the nitrogenous material 350 on the quantum dot 330. The transitory chemical bond will cause an electronic effect 375 (shown in FIG. 10) in the SET 300, due to the charge difference near the quantum dot 330.

Figure 10:
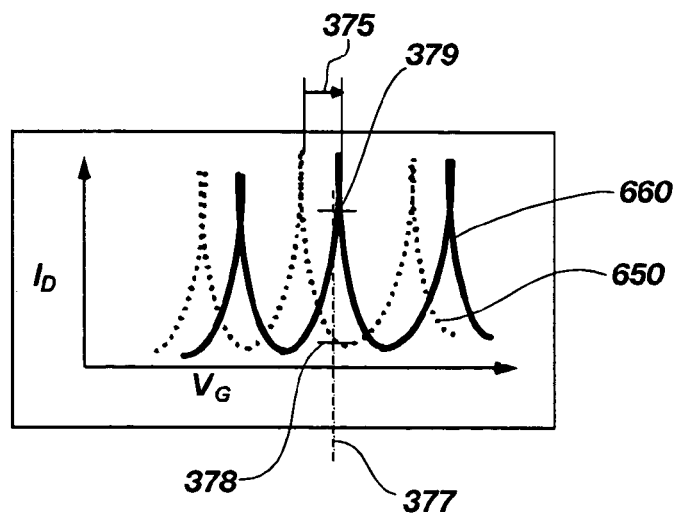
FIG. 10 is a graphical view illustrating an electronic effect on an exemplary single electron transistor sensing a nucleic acid chain.

FIG. 10 illustrates this electronic effect 375 as a gate voltage versus drain current at a fixed source to drain bias level. A first curve 650 (shown as a dotted line) illustrates the SET 300 characteristics before the transitory chemical bond. A second curve 660 (shown as a solid line) illustrates a shift in the characteristics of the SET 300 due to the change in charge near the quantum dot 330. If a gate bias is set at a sampling level where the SET 300 is in a relatively low conductance state 378, the shift in characteristics due to the change in charge near the quantum dot 330 may cause the SET 300 to move to a higher conductance state 379. This higher conductance at the drain 320 may be sensed by other electronic devices on the substrate 302 to give an indication that the transitory chemical bond has taken place. In other words, a C base was, at that time, substantially near the quantum dot 330.

Signal processing hardware, software, or combination thereof, may then be used to gather and process data of the times when C bases are substantially near the quantum dot 330 and the speed of the nucleic acid chain 100. If other molecule sensors 300 are configured in the nanochannel 240, sensitive to the other bases 120 (i.e., A, T, G, and U), a complete solution of the nucleic acid chain 100 may be derived based on the velocity of the nucleic acid chain 100 and the relative positioning of the various molecule sensors 300.

In addition, a DNA molecule is negatively charged and the magnitude of the charge is proportional to the length of the molecule. Thus, because the SET 300 is so sensitive to charge variations, the SET 300 may also be used to determine the molecules overall length and the current position of the molecule relative to the SET 300.

Figure 11:
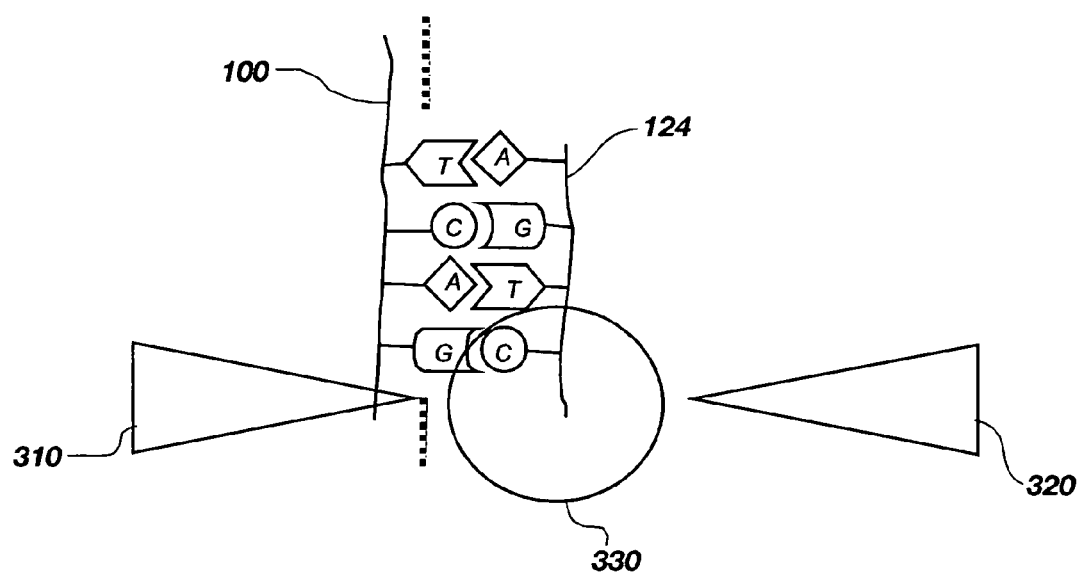
FIG. 11 is a top view of an exemplary single electron transistor including an oligonucleotide disposed on a quantum dot and an exemplary bonding to a nucleic acid chain.

FIG. 11 illustrates the source 310, drain 320, and quantum dot 330 of another exemplary SET 300. The quantum dot 330 in this exemplary SET 300 includes a nitrogenous material comprising an oligonucleotide 124 attached to the quantum dot 330. The oligonucleotide 124 may include many combinations of nucleotides and may have various lengths to comprise a specific combination of nucleotides that may be of interest. By way of example, FIG. 11 illustrates an oligonucleotide 124 including four nucleotides in the series of C, T, G, and A.

The attachment of the oligonucleotide 124 to the SET 300 may be accomplished with a variety of methods know to those of ordinary skill in the art, such as the methods used in micro-arrays using fluorescent tags.

As the nucleic acid chain 100 passes substantially near the attached oligonucleotide 124, if a complementary sequence of bases passes substantially near the attached oligonucleotide 124, a transitory chemical bond (i.e., hybridization) may occur between the oligonucleotide 124 and the complementary sequence on the nucleic acid chain 100. In the exemplary embodiment of FIG. 11, the oligonucleotide 124 comprising the sequence C, T, G, A, may hybridize with the complementary sequence G, A, C, T on the nucleic acid chain 100. As with the single base example of FIG. 9, this transitory chemical bond between the nucleic acid chain 100 and the attached oligonucleotide 124 will cause an electronic effect in the SET 300, due to the charge difference near the quantum dot 330. This electronic effect 375 will be similar to that shown in FIG. 10, but perhaps with a different magnitude, than that for the SET 300 coated with a nitrogenous material 350. A plurality of molecule sensors 300 configured with a variety of oligonucleotides 124 may be useful in determining different specific characteristics of any given nucleic acid chain 100.

The transitory chemical bond results from weak hydrogen bonds between the oligonucleotide 124 on the quantum dot 330, and the nucleic acid chain 100. The transitory chemical bond may be broken, allowing continued transportation of the nucleic acid chain 100, by the motive force causing transportation of the nucleic acid chain 100, thermal energy, optical energy, or combinations thereof.

Figure 12A:
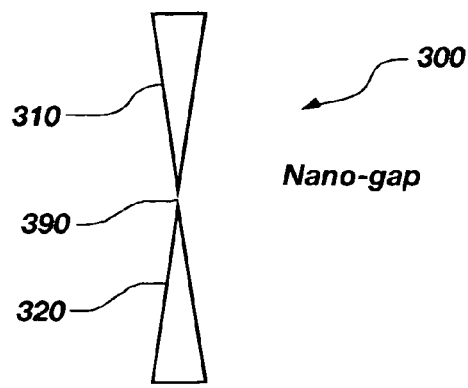
FIGS. 12A, 12B, and 12C are pictorial top views of exemplary single electron transistor including various numbers of quantum dots.
Figure 12B:
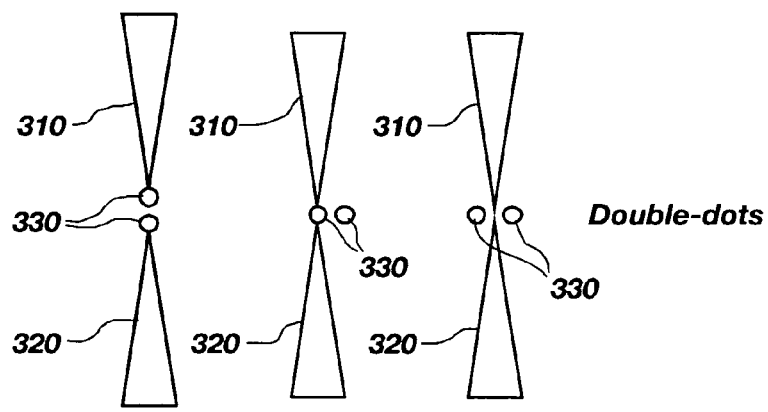
Figure 12C:
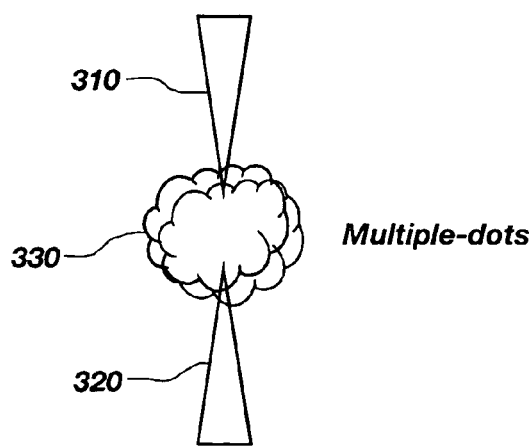

FIGS. 12A, 12B, and 12C illustrate other exemplary molecule sensors 300 in the invention. In some cases, it may be desirable to include two, or more quantum dots 330 between the source 310 and drain 320, as illustrated in FIGS. 12B and 12C. This may increase sensitivity, noise immunity, or combinations thereof. The operation of multiple dot SETs is similar to that described for the single dot SET 300, except that it may be possible to shift the sensing voltage of different quantum dots 330 based on their location relative to gate electrodes. This may generate more sensitivity to shifts in the SET characteristics to a charge substantially near the quantum dots 330.

FIG. 12A is a nanogap implementation of a molecule sensor with no quantum dot and only a single tunneling junction in the gap between the source 310 and drain 320. In the nanogap 390 embodiment, the nitrogenous material 350, or nitrogenous material comprising an oligonucleotide 124, is disposed at the nanogap 390. With this configuration, the charge difference, due to a transitory chemical bond substantially near the nanogap 390, may cause a difference in the tunneling characteristics of the nanogap 390, and, as a result, the current flowing between the source 310 and drain 320.

FIG. 13 illustrates a molecule analysis device with a plurality of molecule sensors 300 coupled by a long nanochannel (not shown) for carrying the nucleic acid chain 100. The embodiment of FIG. 13 may be used to detect a variety of different sequences of interest in the nucleic acid chain 100. For example, the embodiment illustrated in FIG. 13 is configured to detect all the 64 possible combinations of codons. This may be useful for identifying the various amino acids, start codons, and stop codons of a protein. It will be clear to those of ordinary skill in the art that many other useful combinations of molecule analysis devices with various combinations of oligonucleotides 124, nitrogenous material 350, or combination thereof are contemplated with the scope of the present invention.

Of course, it will also be clear that the matrix organization is an arbitrary organization useful for explanation and illustration. However, many other configurations including straight nanochannels, curved nanochannels, serpentine nanochannels, and various organizations of the molecule sensors are contemplated within the scope of the present invention.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A molecular analysis device, comprising:
   a first reservoir:
   a second reservoir;
   a nanochannel configured to carry at least one molecule having one or more nucleotide bases from the first reservoir to the second reservoir, the nanochannel having a cross section less than about 100 nanometers; and
   a molecule sensor located near the nanochannel, the molecule sensor comprising;
      a single electron transistor comprising:
         a first terminal;
         a second terminal;
         a third terminal configured for biasing an electronic effect of the single electron transistor; and
         at least one quantum dot fixed between the first terminal and the second terminal; and
      a nitrogenous material disposed on the at least one quantum dot and configured to form a transitory bond with the at least one molecule as the at least one molecule passes through the nanochannel from the first reservoir to the second reservoir;
   wherein the molecule sensor develops the electronic effect responsive to the transitory bond.

2. The device of claim 1, wherein the transitory bond comprises a transitory chemical bond between the nitrogenous material and the at least one molecule.

3. The device of claim 1, wherein the one or more nucleotide bases comprises at least one base selected from the group consisting of adenine, thymine, uracil, cytosine, and guanine.

4. The device of claim 1, wherein the nitrogenous material comprises at least one base selected from the group consisting of adenine, thymine, uracil, cytosine, and guanine.

5. The device of claim 4, wherein the nitrogenous material further comprises a material selected from the group consisting of a sugar chemically bonded to the base and a sugar-phosphate chemically bonded to the base.

6. The device of claim 1, wherein the nitrogenous material comprises an oligonucleotide and the nucleotide base is a complementary match to the oligonucleotide.

7. The device of claim 1, wherein the electronic effect is a change in electrical charge of the at least one quantum dot indicated by an electrical current change between the first terminal and the second terminal.

8. The device of claim 1, wherein the third terminal comprises a substrate bearing the single electron transistor.

9. The device of claim 1, further comprising at least one electrode disposed substantially near the at least one quantum dot and configured for regulating transportation of the molecule by modifying a voltage potential on the at least one electrode.

10. The device of claim 9, wherein the at least one electrode is further configured for biasing the electronic effect of the single electron transistor.

11. The device of claim 1, wherein the nanochannel comprises:
an entrance point and an exit point; and
a transport medium disposed in the nanochannel for transporting the molecule in a lengthwise fashion through the nanochannel in a transport direction from the entrance point to the exit point to successively present each nucleotide base distributed along the length of the molecule to the nitrogenous material.

12. The device of claim 11, wherein the transport medium near the exit point is positively charged relative to the transport medium near the entrance point.

13. The device of claim 11, wherein the at least one quantum dot is positioned at a location selected from the group consisting of: substantially in the nanochannel between the entrance point and the exit point; external to the nanochannel and substantially near the entrance point of the nanochannel; and external to the nanochannel and substantially near the exit point of the nanochannel.

14. A molecular analysis device, comprising:
at least a first reservoir;
at least a second reservoir;
a plurality of nanochannels each configured to carry one or more molecules having one or more nucleotide bases from the at least a first reservoir to the at least a second reservoir, each nanochannel of the plurality having a cross section less than about 100 nanometers; and
a plurality of molecule sensors, each molecule sensor of the plurality being located near at least one nanochannel of the plurality of nanochannels, each molecule sensor comprising:
a single electron transistor comprising;
a first terminal;
a second terminal;
a third terminal configured for biasing an electronic effect of the single electron transistor; and
at least one quantum dot fixed between the first terminal and the second terminal;
a nitrogenous material disposed on the at least one quantum dot and configured to form a transitory bond with one or more of the molecules having one or more nucleotide bases as the one or more of the molecules passes from the first reservoir to the second reservoir through a nanochannel of the plurality located near the respective molecule sensor;
wherein the molecule sensor develops the electronic effect responsive to the transitory bond.

15. The device of claim 14, further comprising a plurality of nitrogenous materials, each nitrogenous material of the plurality being disposed on the at least one quantum dot of at least one molecule sensor of the plurality of molecule sensors, and wherein each nitrogenous material of the plurality is configured to form the transitory bond with a different identifiable configuration of the molecule.

16. The device of claim 14, wherein the molecule sensors of the plurality are configured to detect a plurality of identifiable configurations.

17. The device of claim 14, wherein the transitory bond comprises a transitory chemical bond between the nitrogenous material and the one or more of the molecules having one or more nucleotide bases.

18. The device of claim 14, wherein the one or more nucleotide bases comprises a base selected from the group consisting of adenine, thymine, uracil, cytosine, and guanine.

19. The device of claim 14, wherein the nitrogenous material disposed on the at least one quantum dot of each molecule sensor of the plurality comprises a base selected from the group consisting of adenine, thymine, uracil, cytosine, and guanine.

20. The device of claim 19, wherein the nitrogenous material further comprises a material selected from the group consisting of a sugar chemically bonded to the base and a sugar-phosphate chemically bonded to the base.

21. The device of claim 14, wherein the nitrogenous material comprises an oligonucleotide configured to form the transitory bond with a complementary match to the oligonucleotide.

22. The device of claim 14, wherein the electronic effect is a change in electrical charge of the at least one quantum dot indicated by an electrical current change between the first terminal and the second terminal.

23. The device of claim 14, wherein the third terminal of each molecule sensor of the plurality comprises a substrate bearing the single electron transistor.

24. The device of claim 14, wherein each molecule sensor further comprises at least one electrode disposed substantially near the at least one quantum dot and configured for regulating transportation of the molecule by modifying a voltage potential on the at least one electrode.

25. The device of claim 24, wherein the at least one electrode is further configured for biasing the electronic effect of the single electron transistor.

26. The device of claim 14, wherein each nanochannel of the plurality comprises:
an entrance point and an exit point; and
a transport medium disposed in the nanochannel for transporting the the one or more molecules in a lengthwise fashion through the nanochannel in a transport direction from the entrance point to the exit point to successively present each nucleotide base distributed along the length of the one or more molecules to the nitrogenous material.

27. The device of claim 26, wherein the transport medium near the exit point is positively charged relative to the transport medium near the entrance point.

28. The device of claim 26, wherein the at least one quantum dot of each molecule sensor of the plurality is positioned at a location selected from the group consisting of: substantially in the nanochannel between the entrance point and the exit point; external to the nanochannel and substantially near the entrance point of the nanochannel; and external to the nanochannel and substantially near the exit point of the nanochannel.

29. A molecular analysis device, comprising:
a first reservoir;
a second reservoir;
a nanochannel configured to carry at least one molecule having one or more nucleotide bases from the first reservoir to the second reservoir, the nanochannel having a cross section less than about 100 nanometers; and
a molecule sensor located near the nanochannel, the molecule sensor comprising:

a first terminal, a second terminal, and a nanogap located between the first terminal and the second terminal; and a nitrogenous material disposed on the nanogap and configured to form a transitory bond with that at least one molecule having one or more nucleotide bases; and at least one electrode disposed at least substantially near the nanogap and configured for regulating transportation of the molecule by modifying a voltage potential on the at least one electrode;

wherein the molecule sensor develops an electronic effect responsive to the transitory bond.

30. The device of claim 29, wherein the transitory bond comprises a transitory chemical bond between the nitrogenous material and the at least one molecule.

31. The device of claim 29, wherein the at least one molecule comprises a base selected from the group consisting of adenine, thymine, uracil, cytosine, and guanine.

32. The device of claim 29, wherein the nitrogenous material comprises a base selected from the group consisting of adenine, thymine, uracil, cytosine, and guanine.

33. The device of claim 32, wherein the nitrogenous material further comprises a material selected from the group consisting of a sugar chemically bonded to the base and a sugar-phosphate chemically bonded to the base.

34. The device of claim 29, wherein the nitrogenous material comprises an oligonucleotide configured to form the transitory bond with a complementary match to the oligonucleotide.

35. The device of claim 29, wherein the electronic effect is a change in electrical current between the first terminal and the second terminal.

36. The device of claim 29, wherein the nanochannel comprises:

an entrance point and an exit point; and a transport medium disposed in the nanochannel for transporting the at least one molecule in a lengthwise fashion through the nanochannel in a transport direction from the entrance point to the exit point to successively present each nucleotide base distributed along the length of the at least one molecule to the nitrogenous material.

37. The device of claim 36, wherein the transport medium near the exit point is positively charged relative to the transport medium near the entrance point.

38. The device of claim 36, wherein the nanogap is positioned at a location selected from the group consisting of: substantially in the nanochannel between the entrance point and the exit point; external to the nanochannel and substantially near the entrance point of the nanochannel; and external to the nanochannel and substantially near the exit point of the nanochannel.

* * * * *

UNITED STATES PATENT AND TRADEMARK OFFICE
CERTIFICATE OF CORRECTION

PATENT NO. : 7,947,485 B2
APPLICATION NO. : 11/144586
DATED : May 24, 2011
INVENTOR(S) : Wei Wu et al.

It is certified that error appears in the above-identified patent and that said Letters Patent is hereby corrected as shown below:

In column 16, line 42, in Claim 26, delete "the the" and insert -- the --, therefor.

Signed and Sealed this
Sixth Day of December, 2011

David J. Kappos
*Director of the United States Patent and Trademark Office*